US012648831B2

(12) United States Patent
Elimelech et al.

(10) Patent No.: US 12,648,831 B2
(45) Date of Patent: Jun. 9, 2026

(54) REGISTRATION OF A FIDUCIAL MARKER FOR AN AUGMENTED REALITY SYSTEM

(71) Applicant: AUGMEDICS LTD., Yokneam Illit (IL)

(72) Inventors: Nissan Elimelech, Beerotaim (IL); Stuart Wolf, Yokneam (IL)

(73) Assignee: Augmedics, LTD, Yokneam Illit (IL)

( * ) Notice: Subject to any disclaimer, the term of this patent is extended or adjusted under 35 U.S.C. 154(b) by 0 days.

(21) Appl. No.: 19/170,933

(22) Filed: Apr. 4, 2025

(65) Prior Publication Data

US 2025/0288388 A1     Sep. 18, 2025

Related U.S. Application Data

(63) Continuation of application No. 18/632,588, filed on Apr. 11, 2024, now Pat. No. 12,290,416, which is a continuation of application No. 17/045,766, filed as application No. PCT/IB2019/053524 on Apr. 30, 2019, now Pat. No. 11,980,507.

(60) Provisional application No. 62/665,541, filed on May 2, 2018.

(51) Int. Cl.
    *A61B 90/00*     (2016.01)
    *A61B 34/20*     (2016.01)
(52) U.S. Cl.
    CPC .............. *A61B 90/39* (2016.02); *A61B 34/20* (2016.02); *A61B 2034/2055* (2016.02); *A61B 2090/365* (2016.02); *A61B 2090/3916* (2016.02); *A61B 2090/3937* (2016.02); *A61B*

*2090/3966* (2016.02); *A61B 2090/3983* (2016.02); *A61B 2090/3991* (2016.02); *A61B 2090/3995* (2016.02)

(58) Field of Classification Search
    CPC ...... A61B 2090/365; A61B 2090/3916; A61B 2090/3983; A61B 2090/3966; A61B 2090/3937; A61B 2090/3991; A61B 2090/3995
    See application file for complete search history.

(56) References Cited

U.S. PATENT DOCUMENTS

2013/0345718 A1 * 12/2013 Crawford ............... A61B 34/30
                                                                     606/130
2015/0230873 A1 * 8/2015 Kubiak .................. A61B 6/583
                                                                     378/205

FOREIGN PATENT DOCUMENTS

WO      2018/073452 A1     4/2018

OTHER PUBLICATIONS

European Patent Office, Communication Pursuant to Article 94(3) EPC for EP Patent Application No. 19796580.9, dated Oct. 1, 2025, 4 pages.

* cited by examiner

*Primary Examiner* — Joel F Brutus
(74) *Attorney, Agent, or Firm* — Dinsmore & Shohl LLP

(57) ABSTRACT

A registration marker comprising a radiotransparent substrate and a pattern formed in at least two dimensions, which is disposed on the substrate and is optically visible. The registration marker also has a multiplicity of radiopaque elements, which are disposed in the substrate and are spatially arranged in at least two dimensions to provide a unique pattern.

20 Claims, 5 Drawing Sheets

REGISTRATION OF A FIDUCIAL MARKER FOR AN AUGMENTED REALITY SYSTEM

CROSS-REFERENCE TO RELATED APPLICATIONS

This application is a continuation of U.S. application Ser. No. 18/632,588, filed on Apr. 11, 2024, which is a continuation of U.S. application Ser. No. 17/045,766, filed on Oct. 7, 2020, which is a national stage entry of International PCT Application No. PCT/IB2019/053524, filed on Apr. 30, 2019, which claims the benefit of U.S. Provisional Patent Application 62/665,541, filed May 2, 2018, each of which is incorporated herein by reference in its entirety.

FIELD OF THE INVENTION

This invention relates generally to an augmented reality system, and specifically to accurate registration of different elements operating in the system when it is used for a medical procedure.

BACKGROUND OF THE INVENTION

For a medical professional to use an augmented reality system during a medical procedure, typically with a purpose built head mounted display, some images presented to the professional on the display may need to be aligned with the patient undergoing the procedure. Although some misalignment may be acceptable, for satisfactory presentation of the images the misalignment may typically not be more than about 2-3 mm. Ensuring such a limit on the misalignment requires accurate registration of the patient's anatomy with the presented images.

If the medical procedure involves surgery exposing internal elements of the patient, the registration typically involves registration of patient images determined in different modalities, in which case the misalignment should be typically 2 mm or less. For example, depending on the procedure being performed, internal patient elements such as bones may be imaged using a first modality comprising computerized tomography (CT) imaging, while the augmented reality system presents these elements optically, i.e., using a second modality.

However, the required registration may not be simple to achieve, because of limitations of the imaging systems. In the above example, the CT imaging modality may have a limited field of view, so that it is unable to simultaneously image a tracking patient marker (required for the optical augmented reality system) and patient bones such as the spine. An optical imaging modality is unable to simultaneously image the patient marker and the spine, since the latter is invisible.

U.S. Pat. No. 7,556,428, to Sukovic et al. describes a surgical navigation system that is claimed to overcome the problem of the narrow field of view of a CT scanner. A patient tracker, having locators, is positioned on the patient, typically on the patient's forehead, and a tracking system tracks the positions and orientations of the locators. Sukovic states that a "registration appendage" includes radio-opaque markers, and may be "removably secured to the patient tracker in a known position and orientation relative to the patient tracker". Sukovic further states that "When the locators of the patient tracker are positioned outside of the field of view of the CT scanner, the registration appendage can be secured to the patient tracker."

As is apparent from Sukovic's disclosure, the patient tracker and registration appendage relative positions must initially be known, and the two elements need to be physically secured together in order for Sukovic's system to function. Both of these requirements introduce limitations into the functioning of Sukovic's surgical navigation system.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a registration marker, including:

a radiotransparent substrate;

a pattern formed in at least two dimensions, which is disposed on the substrate and is optically visible; and a multiplicity of radiopaque elements, which are disposed in the substrate and are spatially arranged in at least two dimensions to provide a unique pattern.

In a disclosed embodiment the optically visible pattern and/or said unique pattern have no axis of symmetry and no plane of symmetry.

In a further disclosed embodiment the radiotransparent substrate is optically opaque and includes a surface, and the pattern is fixedly mounted on the surface.

In a yet further disclosed embodiment the pattern includes optically reflective discrete elements fixedly mounted on the surface. The discrete elements may have a common size and shape, and locations of the discrete elements are selected to form the pattern.

The discrete elements may consist of a given discrete element and remaining discrete elements having a common size, wherein the given discrete element has a different size from the remaining discrete elements.

Alternatively or additionally the discrete elements may consist of a given discrete element and remaining discrete elements having a common shape, wherein the given discrete element has a different shape from the remaining discrete elements.

In an alternative embodiment the substrate includes a pillar attached to a rectangular parallelepiped, and the pattern includes optically reflective discrete elements, wherein one of the discrete elements is mounted on the pillar.

In a further alternative embodiment the substrate includes an indentation formed within a rectangular parallelepiped, and the pattern includes optically reflective discrete elements, wherein one of the discrete elements is mounted on a surface of the indentation.

The pattern may be formed in two dimensions. Alternatively the pattern may be formed in three dimensions.

The radiopaque elements may be spatially arranged in two dimensions. Alternatively the radiopaque elements may be spatially arranged in three dimensions.

The radiopaque elements may have a common size and shape, and locations of the radiopaque elements may be selected to form the unique pattern.

The radiopaque elements may consist of a given radiopaque element and remaining radiopaque elements having a common size, and the given radiopaque element may have a different size from the remaining radiopaque elements.

The radiopaque elements may consist of a given radiopaque element and remaining radiopaque elements having a common shape, and the given radiopaque element may have a different shape from the remaining radiopaque elements.

There is further provided, according to an embodiment of the present invention a method, including:

providing a radiotransparent substrate;

disposing a pattern formed in at least two dimensions and which is optically visible on the substrate; and disposing in the substrate a multiplicity of radiopaque elements, the elements being spatially arranged in at least two dimensions to provide a unique pattern.

There is further provided, according to an embodiment of the present invention, a method for registering a patient marker with a skeleton of a patient, including:

attaching the patient marker to a portion of the skeleton, the patient marker having a patient marker frame of reference;

providing a registration marker, including:

a radiotransparent substrate;

a pattern formed in at least two dimensions, which is disposed on the substrate and is optically visible, and which has no axis of symmetry and no plane of symmetry; and a multiplicity of radiopaque elements, which are disposed in the substrate and are spatially arranged in at least two dimensions to have no axis of symmetry and no plane of symmetry;

positioning the registration marker in proximity to the patient marker;

analyzing an optical image of the registration marker and the patient marker to determine a first relation between the patient marker frame of reference and a registration marker frame of reference;

analyzing a fluoroscopic image of the registration marker and the skeleton of the patient to determine a second relation between the registration marker frame of reference and the skeleton of the patient; and using the first and second relations to formulate a registration relation between the patient marker and the skeleton.

There is further provided, according to an embodiment of the present invention, apparatus, including:

a patient marker configured to be attached to a portion of a skeleton of a patient, the patient marker having a patient marker frame of reference;

a registration marker, including:

a radiotransparent substrate, a pattern formed in at least two dimensions, which is disposed on the substrate and is optically visible, and which has no axis of symmetry and no plane of symmetry, and a multiplicity of radiopaque elements, which are disposed in the substrate and are spatially arranged in at least two dimensions to have no axis of symmetry and no plane of symmetry; and a processor, configured to:

analyze an optical image of the patient marker and the registration marker, positioned in proximity to the patient marker, so as to determine a first relation between the patient marker frame of reference and a registration marker frame of reference, analyze a fluoroscopic image of the registration marker and the skeleton of the patient to determine a second relation between the registration marker frame of reference and the skeleton of the patient, and

use the first and second relations to formulate a registration relation between the patient marker and the skeleton.

The present disclosure will be more fully understood from the following detailed description of the embodiments thereof, taken together with the drawings. A brief description of the drawings follows.

DETAILED DESCRIPTION OF EMBODIMENTS

Overview

Figure 1:
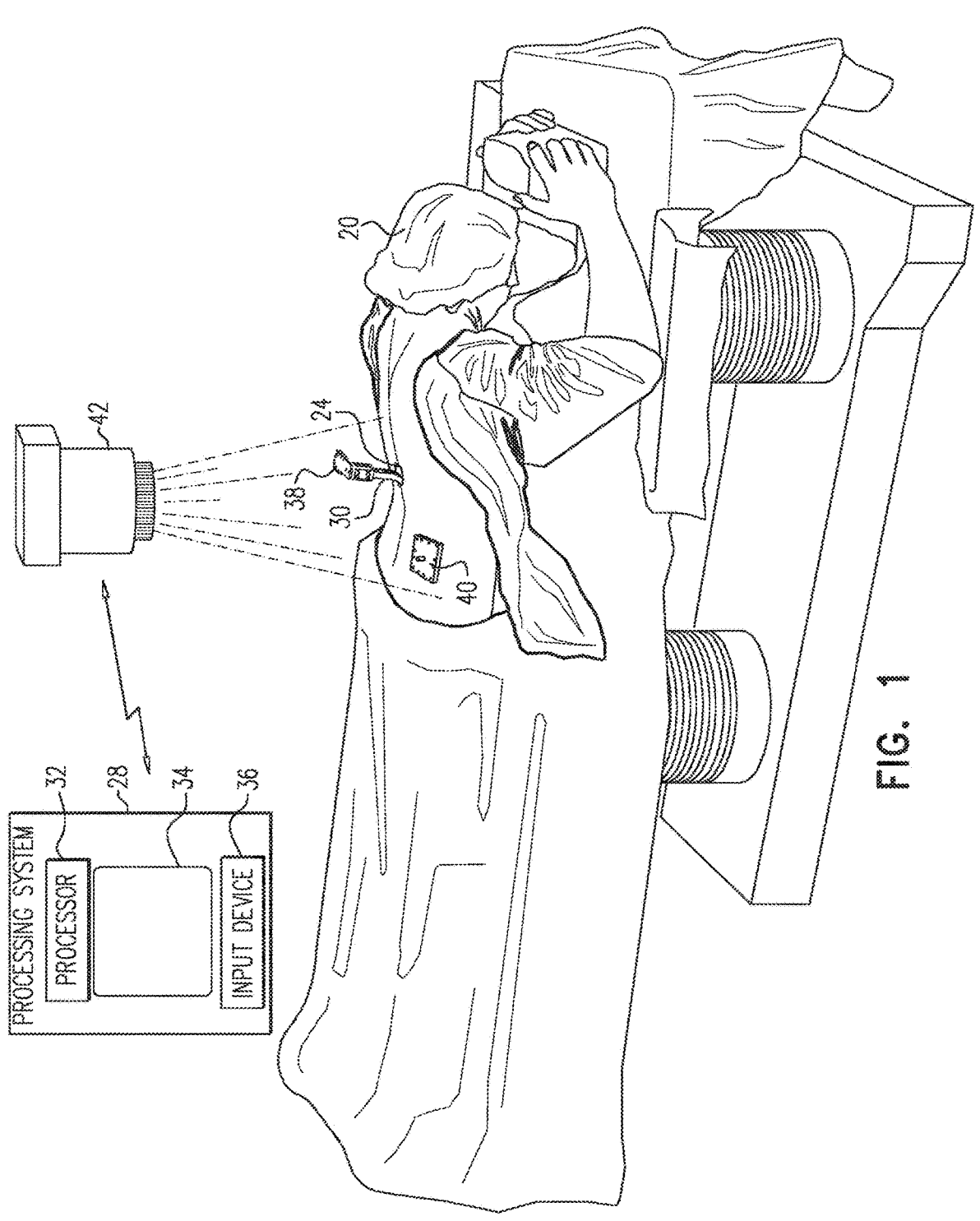
FIG. 1 is a schematic illustration of an initial preparatory stage of a medical procedure, according to an embodiment of the present invention.

Embodiments of the present invention overcome the problem of a narrow field of view of a fluoroscopic imaging system, such as a CT scanner, by using a patient marker and a registration marker, where the latter may be located in substantially any position relative to the former, and where the markers are not physically connected.

As described in more detail below, embodiments of the present invention provide a system for accurately registering a patient marker, visible in a first, optical, modality, that is attached to a spinous process of a patient, visible in a second, fluoroscopic, modality. The registration is performed during an initial stage of a procedure on the spine of the patient. In order to provide such accurate registration, embodiments of the invention use a registration marker which is configured to be visible in both modalities, i.e., both optically and under fluoroscopic imaging.

The registration marker comprises a radiotransparent substrate upon which a pattern, which is optically visible, is disposed. The pattern is configured to be in at least two dimensions, i.e., it may be formed in two dimensions or in three dimensions. Said pattern is unique and provides an unambiguous position and frame of reference of the registration marker. According to a preferred embodiment, said pattern is configured to have no axis of symmetry and no plane of symmetry. Alternatively, said unique pattern may be provided by optically reflective elements of different shapes and/or sizes so that an optical image of the pattern provides an unambiguous position and orientation of a frame of reference (FOR) of the registration marker.

The registration marker also comprises a multiplicity of radiopaque elements which are disposed in the substrate. The radiopaque elements are spatially arranged to be in at least two dimensions, i.e., the elements may be arranged to be in two dimensions or to be in three dimensions. As for the pattern described above, the pattern disposed by said radiopaque elements is unique and provides an unambiguous position and frame of reference of the registration marker. According to a preferred embodiment, the arrangement of the radiopaque elements also has no axis of symmetry and no plane of symmetry, so that a fluoroscopic image of the substrate provides the unambiguous position and orientation of the FOR of the registration marker. Alternatively, said unique pattern may be provided by radiopaque elements of different shapes and/or sizes.

In the initial stage of the procedure, the patient marker is clamped to a patient spinous process, and the registration marker is placed on the patient's back in proximity to the marker.

A fluoroscopic image of the registration marker and the patient's spine is acquired, and a first relation between a registration marker FOR and the spine is formulated from the image. For the fluoroscopic image acquisition, only the registration marker and the patient's spine are visible to the fluoroscope. As is explained further below, only the registration marker is subject to fluoroscopy. The patient marker is not subject to fluoroscopy.

In addition, a camera acquires an optical image of the patient marker and the registration marker, and a second relation between the registration marker FOR and the patient marker is formulated. For the optical image, only the registration marker and the patient marker are visible to the camera.

The two relations are then combined to provide an accurate relation registering the patient marker with the patient spine.

The relation found may be used by an augmented reality system operated in a medical procedure on the spine of the patient, for example by presenting vertebrae images that are accurately registered with the actual vertebrae.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 3:
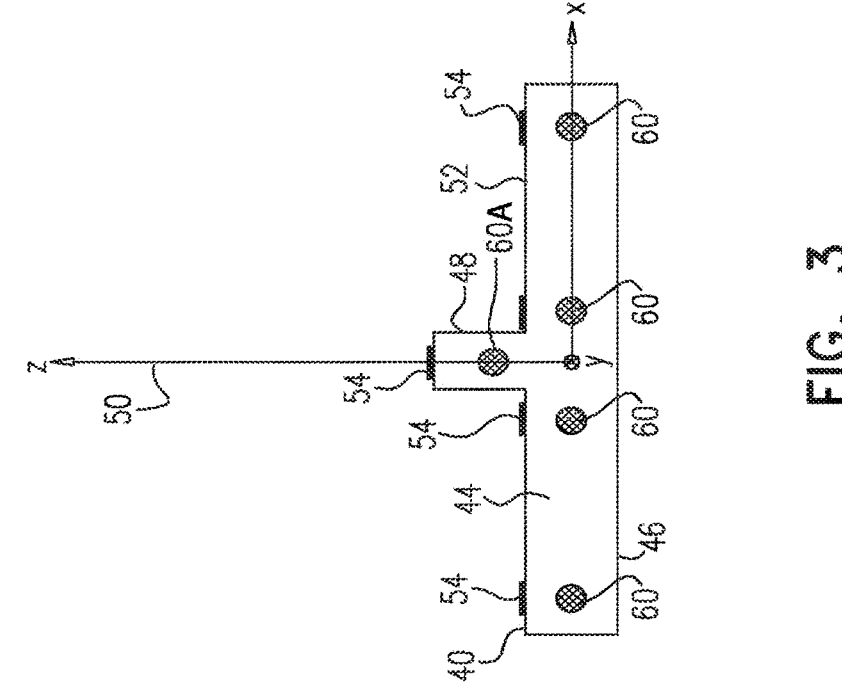
FIGS. 2, 3, and 4 are schematic depictions of entities used in the initial stage, according to an embodiment of the present invention.
Figure 2:
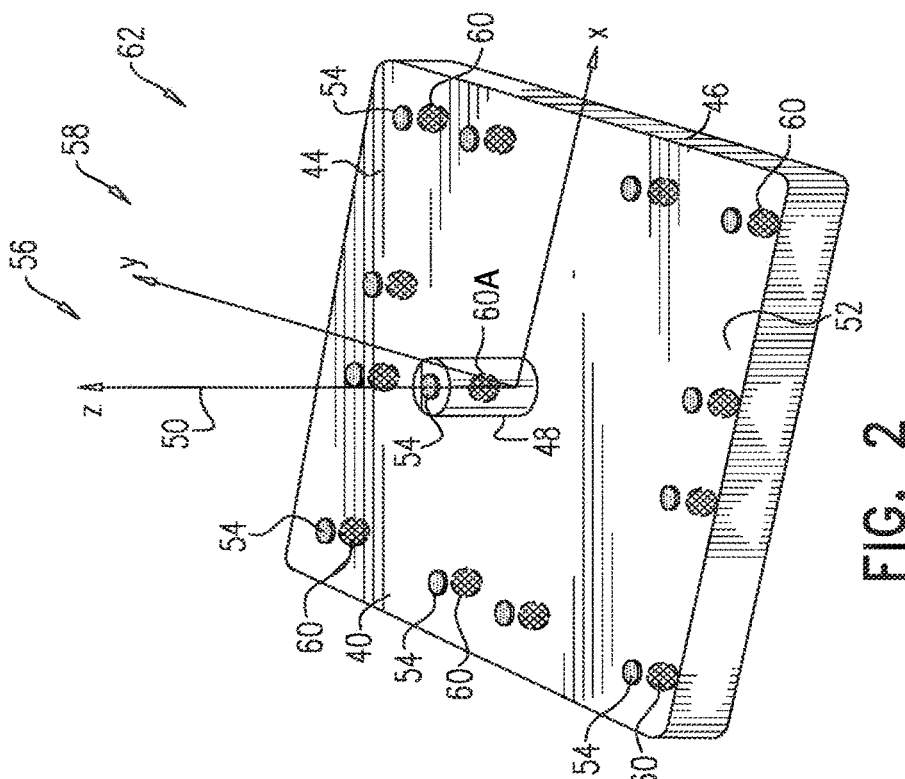
Figure 4:
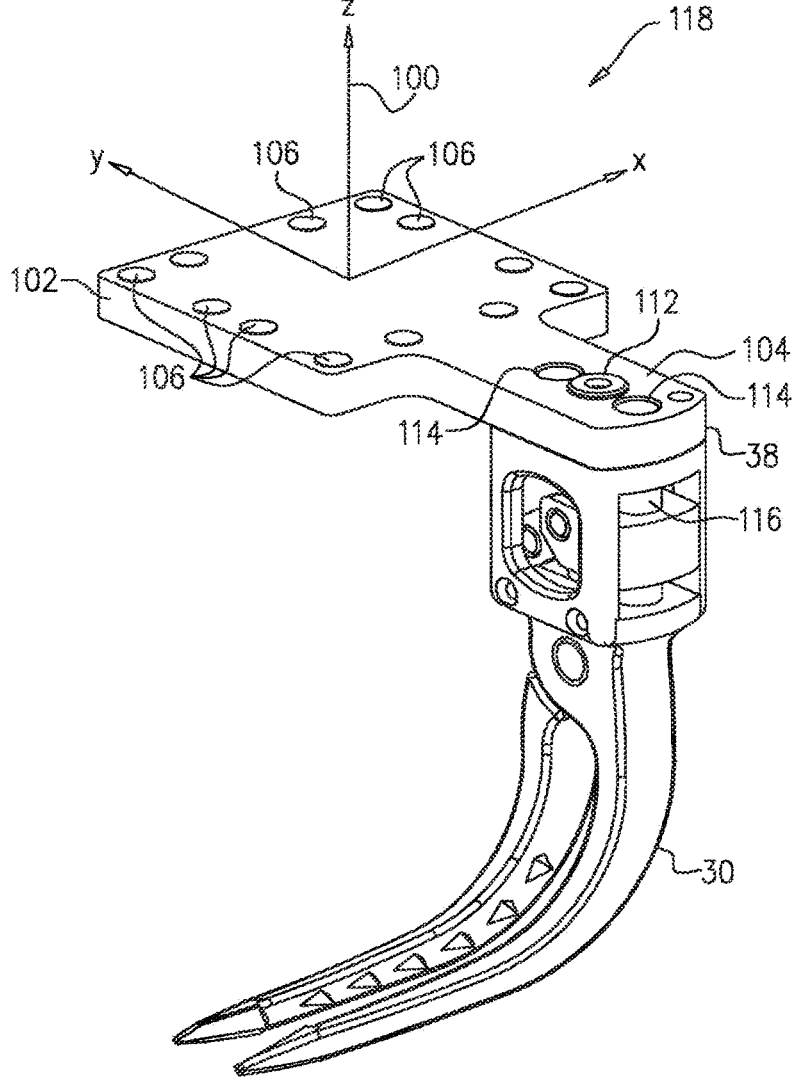

Reference is now made to FIGS. 1, 2, 3, and 4, which are diagrams according to an embodiment of the present invention. FIG. 1 is a schematic illustration of an initial preparatory stage of a medical procedure, and FIGS. 2, 3, and 4 are schematic depictions of entities used in the initial stage. The medical procedure exemplified here is performed on the back of a patient 20, and during the initial stage of the procedure a medical professional (not shown in FIG. 1) makes an incision 24 into the patient's back. The professional inserts a spinous process clamp 30 into the incision, so that opposing jaws of the clamp are located on opposite sides of the spinous processes. The professional then slides the clamp over the vertebral laminas, and adjusts the clamp to grip one or more spinous processes, selected by the professional, of the patient. Clamp 30 is described below with reference to FIG. 4, and a clamp such as clamp 30 is described in more detail in U.S. Provisional Patent Application 62/595,598 which is incorporated herein by reference.

Clamp 30 acts as a support for a patient marker 38, which is attached rigidly to the clamp. During substantially all of the procedure, i.e., during the initial, as well as the subsequent stages, patient marker 38 is used as a fiducial for patient 30, since because of its rigid connection to the patient, any movement of the patient is reflected in a corresponding motion of the patient marker. In order to operate as such a fiducial, in embodiments of the present invention, in the initial stage of the procedure marker 38 is registered with the anatomy of patient 30, herein assumed to comprise the skeleton of the patient, as is described herein.

During the initial stage of the procedure, a registration marker 40 is placed on the patient's back, and is used to implement the registration of patient marker 38 with the anatomy of patient 30. In contrast to patient marker 38, registration marker 40 is typically only used during the initial stage of the procedure, i.e., for the registration of the patient marker 38, and once the registration has been performed, for the subsequent procedure stages the registration marker may be removed from the patient's back. As will be apparent from the following description, only registration marker 40 is subject to fluoroscopy, and patient marker 38 is not subject to fluoroscopy.

Also during the initial stage of the procedure, a camera 42 is used to image the registration marker and the patient marker. The camera is positioned so as to be able to image the positions of the registration marker and the patient marker, and so that neither marker occludes the other. As is explained below, the image of the registration marker and the patient marker formed by camera 42 is used to register patient marker 38 with the anatomy of patient 30. In one embodiment camera 42 is mounted on a head mounted display worn by the medical professional referred to above, for instance, on the head-mounted display 184 described with reference to FIG. 6 below. However, other arrangements for camera 42, so that as imaged by the camera neither marker occludes the other are also considered to be within the scope of the present invention.

Camera 42 typically operates in the visible and/or near-visible spectrum, i.e., at wavelengths of approximately 300 nm-900 nm.

A processing system 28 is coupled, by cables and/or wirelessly, to camera 42. System 28 comprises a computer processor 32, a screen 34, and an input device 36 such as a pointing device, and the system is configured to analyze the images acquired by the camera, as is described further below. Other functions of system 28 are also described below.

FIGS. 2 and 3 are respectively schematic perspective and cross-sectional views of registration marker 40, which is assumed to define a registration marker frame of reference 50, herein assumed to comprise an orthogonal set of xyz axes. Marker 40 is formed from a solid substrate 44, which is opaque to light in the visible and near-visible spectrum, and which is transparent to fluoroscopic radiation. Substrate 44 is typically formed from a hard plastic, such as polycarbonate, but any other solid material which is opaque to light and transparent to fluoroscopic radiation may be used in embodiments of the present invention.

In the illustrated embodiment of marker 40, substrate 44 is formed as a rectangular parallelepiped 46, upon which is mounted a pillar 48.

A plurality of optically reflective, but radiotransparent, discrete elements 54 are disposed on substrate 44. Elements 54 are hereinbelow, by way of example, assumed to comprise discs, and are also referred to herein as discs 54. It is understood that said optically reflective and radiotransparent elements may be of different shapes and/or sizes.

Some of the plurality of discs 54 are fixedly attached, typically by cementing, to a two-dimensional (2D) surface 52 of parallelepiped 46. These discs 54 are formed in a generally rectangular 2D pattern on surface 52. In addition, an optically reflective disc 54 is also cemented onto pillar 48, so that there is in totality a three-dimensional (3D) array of discs 54 disposed on the substrate. The 3D array of discs 54 are distributed on 2D surface 52, and on pillar 48, so that when marker 40 is illuminated and imaged by camera 50 the discs are easily distinguished from substrate 44. Furthermore, as explained in more detail below, the arrangement of discs 54 are configured to enable processor 32 to unambiguously determine the orientation and position of frame of reference 50 from the marker image.

The distributed discs 54 are herein assumed to comprise an optical component 56 of marker 40 that forms an optical pattern 58 for the marker. In a particular aspect of the invention optical pattern 58, comprising the distribution of discs 54, is implemented so that the pattern has no axis of symmetry and no plane of symmetry. The absence of both an axis and a plane of symmetry in the pattern ensures that the unambiguous determination of the orientation and position of the frame of reference of marker 40 is possible from the marker image for multiple different orientations and positions of the marker, the positions being typically within a region approximately 20 cm from the patient marker.

The description above of optical pattern 58 assumes that discs 54 are configured in three dimensions. However, as long as the pattern has no axis of symmetry and no plane of symmetry, the discs forming the pattern may be arranged in only two dimensions, for example, absent the disc on pillar 48. Thus, pattern 58 may be formed in at least two dimensions, i.e., in the case of discs 54, as a two-dimensional array of the discs or as a three-dimensional array of the discs.

It will be understood that the requirement for discs 54 to be arranged to form a pattern having an absence of both an axis and a plane of symmetry may be achieved using discs of substantially the same size and shape, wherein locations of the discs are selected so that the locations are arranged to have the absence of both an axis and a plane of symmetry. The described pattern is hereinbelow referred to as a unique optical pattern.

Alternatively, the unique optical pattern may be achieved using discs of different sizes and/or shapes. In this case, the locations of the discs may also satisfy the requirement, but this is not a necessity.

A multiplicity of radiopaque elements 60 are disposed in substrate 44 by being embedded in a distribution within parallelepiped 46. The distribution of elements 60 is arranged in a two dimensional radiopaque pattern 62 such that, as for the pattern of discs 54, the radiopaque pattern has no axis of symmetry and no plane of symmetry. Because substrate 44 is radiotransparent, and because of the absence of both an axis and a plane of symmetry in radiopaque pattern 62, a fluoroscopic, typically computerized tomography (CT), scan of the radiopaque elements of marker 40 enables the orientation and position of frame of reference 50 to be unambiguously determined by processor 32 from the fluoroscopic scan. In one embodiment elements 60 comprise spheres which are distributed in a 2D generally rectangular 2D pattern that is substantially the same as the rectangular pattern of discs 54 on surface 52.

The description above of elements 60 assumes that they are arranged in a radiopaque pattern of two dimensions. However, as long as the pattern has no axis of symmetry and no plane of symmetry, the elements forming the pattern may also be arranged in three dimensions, for example, by incorporation of a radiopaque element 60A, substantially similar to elements 60, in pillar 48. Thus, pattern 62 may also be formed in at least two dimensions, i.e., in the case of elements 60 and 60A, as a two-dimensional array of elements 60 or as a three-dimensional array of elements 60 and 60A.

As for discs 54, it will be understood that the requirement for elements 60 to be arranged to form a pattern having an absence of both an axis and a plane of symmetry may be achieved using elements of substantially the same size and shape, wherein locations of the elements are selected so that the locations are arranged to have the absence of both an axis and a plane of symmetry. The described pattern is hereinbelow referred to as a unique radiopaque pattern.

Alternatively, the unique radiopaque pattern may be achieved using elements of different sizes and/or shapes. In this case, the locations of the elements may also satisfy the requirement, but this is not a necessity.

The X-ray wavelengths of the CT scan are assumed to be in a range of 0.01-10 nm.

The above description of marker 40 assumes that discs 54 and elements 60 have different functionalities—the discs being optically reflective and radiotransparent, and the elements being radiopaque. In an alternative embodiment of marker 40 at least some of discs 54 are configured to have dual functionality by being optically reflective and radiopaque. As for the embodiment described above, in the alternative embodiment discs 54 are configured and distributed on substrate 44 so that an optical image of marker 40 provides an unambiguous determination of the orientation and position of frame of reference 50, and a fluoroscopic scan of the marker also provides an unambiguous determination of the orientation and position of the frame of reference.

The physical construction of the illustrated embodiment of marker 40, as a pillar attached to a rectangular parallelepiped, comprising an array of discs 54 and an array of elements 60, is but one example of possible physical constructions of the marker that enables an unambiguous determination of the marker's position and orientation from a camera image and from a fluoroscopic scan. In a disclosed embodiment, rather than marker 40 comprising pillar 48 mounted on substrate 44, an indentation (in place of the pillar) is formed within the substrate, and a disc 54 is located on a surface of the indentation.

Other suitable constructions for marker 40 are also considered to be within the scope of the present invention.

For example, the substrate of marker 40, rather than being formed from a parallelepiped with a pillar or an indentation, may be formed as substantially any conveniently shaped solid object that is opaque to light in the visible and near-visible spectrum and which is transparent to fluoroscopic radiation.

In addition, rather than the optical component of marker 40 being comprised of a plurality of discs 54 arranged in a particular pattern, the component may comprise any array or pattern of optical elements that is attached to the substrate, that is diffusely and/or specularly reflective, and that is configured to have the absence of axes and planes of symmetry described above, so that when imaged in visible or near-visible light an unambiguous determination of the marker's position and orientation may be made.

Referring to FIG. 4, patient marker 38 is assumed to define a patient marker frame of reference 100, assumed to comprise an orthogonal set of xyz axes. In the embodiment illustrated in FIG. 4 marker 38 comprises a rectangular parallelepiped substrate 102 to which is attached a tongue 104 used to fixedly connect the substrate to clamp 30. The connection to clamp 30 is by a removable screw 112, and the patient marker connects in a predetermined fixed spatial relationship to the clamp using holes 114 which align with studs 116 of the clamp. Substrate 102 comprises a solid opaque material, and may be formed from any convenient material such as polyimide plastic.

In some embodiments, patient marker 38 may be connected to clamp 30 in more than one fixed spatial relationship. For example, in the embodiment illustrated in FIG. 4, marker 38 may be removed from the clamp, and then reattached to the clamp using screw 112 after being rotated 180° around an axis parallel to the illustrated z axis. It will be understood that holes 114 and mating studs 116 accommodate the two possible fixed spatial relationships. Other mechanical arrangements allowing for the connection of marker 38 to clamp 30 in a plurality of predetermined fixed spatial relationships are assumed to be comprised within the scope of the present invention.

A plurality of optically reflective discs 106, generally similar to discs 54, are attached, typically by cementing, to an upper 2D surface 110 of substrate 102. Discs 106 are formed in a generally rectangular 2D pattern on surface 110. Discs 106 are distributed so that when illuminated and imaged by camera 42 they are easily distinguished from substrate 102, and so that an optical pattern 118 formed by the discs enables processor 32 to unambiguously determine the orientation and position of frame of reference 100 from the camera image. As for discs 54, discs 106 are typically distributed so that they have no axis or plane of symmetry.

In FIG. 4 discs 106 are shown as being distributed on sides of a rectangle, however, it will be understood that this is but one example for the positioning of the discs on surface 110. Other distributions of discs 106 providing, from their images, unambiguous determination of the orientation and position of frame of reference 100 are also assumed to be comprised within the scope of the present invention.

Furthermore, it will be appreciated that the physical construction of patient marker 38 described above is by way of example. Thus, embodiments of the present invention comprise any patient marker formed of any conveniently shaped solid opaque substrate to which is attached an optical pattern, the pattern enabling processor 32 to unambiguously determine the orientation and position of a frame of reference of the marker from a camera image of the optical pattern. As for the example described above with reference to FIG. 4, such a patient marker may be configured to be attached to clamp 30 in a plurality of predetermined fixed spatial relationships with the clamp.

Figure 5:
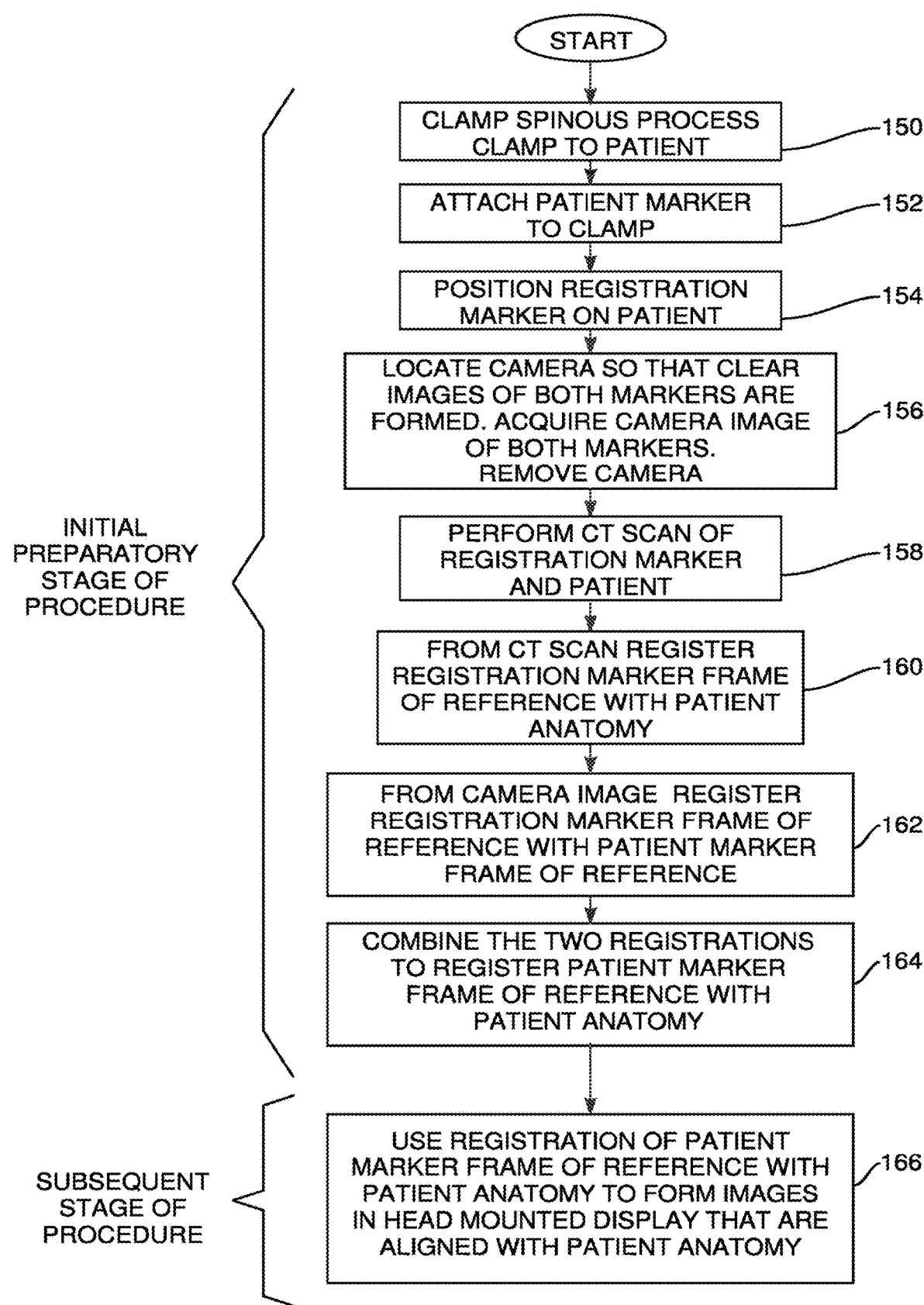
FIG. 5 is a flowchart of steps performed to register a patient marker with the anatomy of a patient during the initial preparatory stage.
Figure 6:
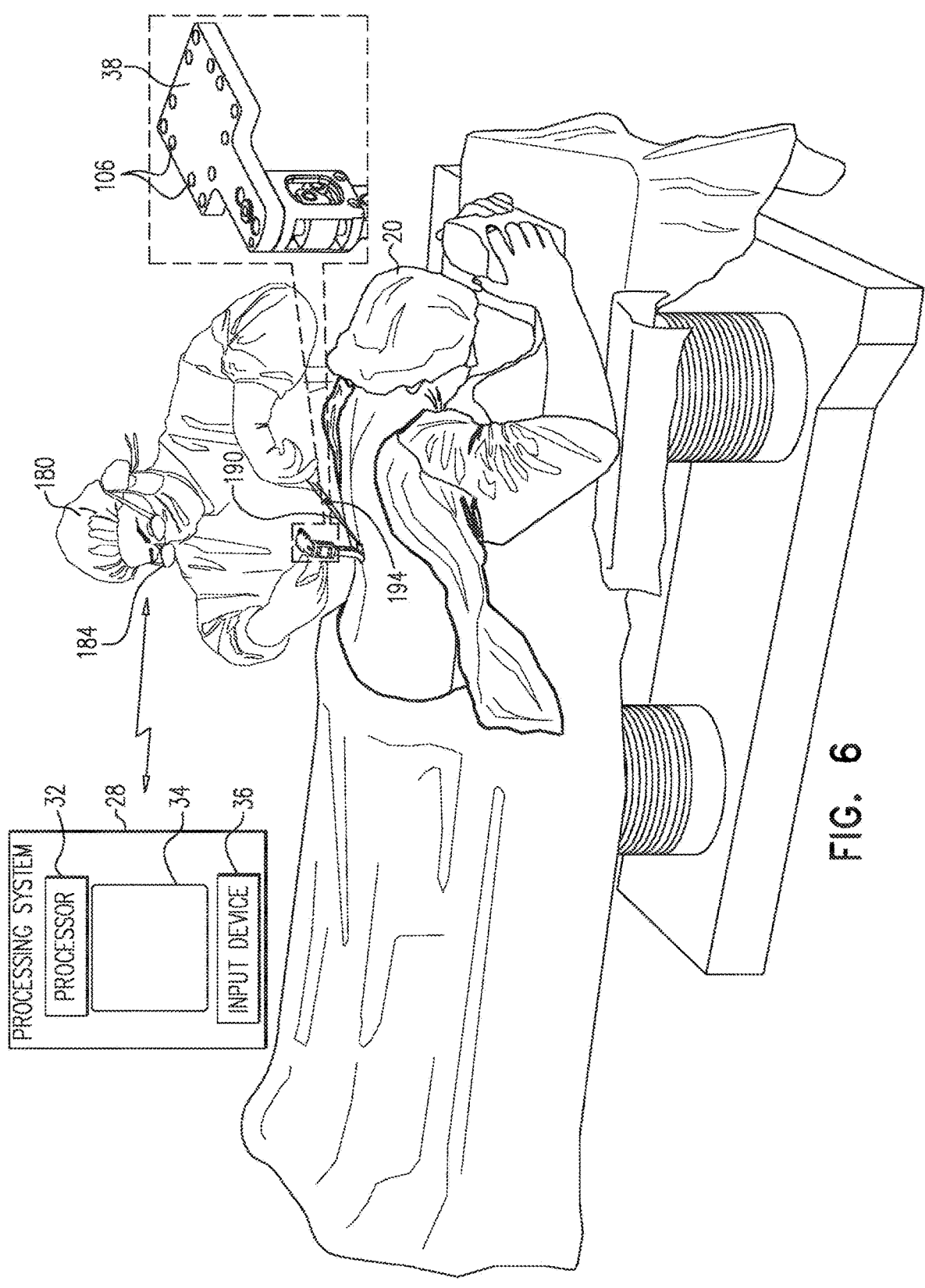
FIG. 6 is a schematic illustration of a subsequent stage of the procedure, according to an embodiment of the present invention.

FIG. 5 is a flowchart of steps performed to register patient marker 38 with the anatomy of patient 20 during the initial preparatory stage of a medical procedure, and FIG. 6 is a schematic illustration of a subsequent stage of the procedure, according to an embodiment of the present invention. Except as otherwise stated, in the following description the steps of the flowchart are assumed to be performed during the initial preparatory stage of the medical procedure, as described above. In addition, while the following description assumes a CT scan, other types of fluoroscopic imaging are also considered to be within the scope of the present invention.

In an initial step 150, a medical professional makes an incision in the back of patient 20, inserts spinous clamp 30 into the patient, and then clamps the clamp to one or more of the processes of the patient.

In a patient marker step 152, the medical professional attaches patient marker 38 to spinous clamp 30, ensuring that the marker is rigidly attached to the clamp.

In a registration marker step 154, the professional places registration marker 40 on the skin of the back of the patient, typically as close to the patient's spine as is convenient.

In a camera step 156, camera 42 images the registration marker and the patient marker. The camera is positioned so that the images it forms of the registration marker and of the patient marker are clear images, i.e., that neither markers occlude the other. If necessary, the professional may adjust the position of the camera (which may be mounted on head-mounted display 184) and/or the registration marker so that clear and acceptable images of both markers are acquired. Typically processor 32 of processing system 28 is configured to verify the acceptability of the two marker images, and if necessary the professional may use and communicate with system 28 to adjust, in an iterative manner, the positions of the camera and the registration marker until system 28 provides an indication to the professional that acceptable images are being generated.

Once acceptable images are being generated, a camera image of the two markers is acquired, and is provided to processing system 28. Camera 42 may then be removed from proximity to patient 20.

In a fluoroscopic scan step 158, a CT scan of patient 20, in the vicinity of marker 40 is performed, and processing system 28 acquires the scan. The scan may be performed by inserting patient 20 into a CT scanning system so that marker 40 is scanned. The insertion may be implemented by bringing the CT scanning system to patient 20, or by transporting the patient to the system. In either case, marker 40 remains in the marker's position of step 156.

In a scan analysis step 160, processor 32 analysis the CT scan acquired in step 158, the scan comprising an image of radiopaque elements 60 and of the anatomy of patient 20. From the acquired image, processor 32 calculates the position and orientation of registration marker frame of reference 50, and registers the frame of reference with the anatomy of the patient. The registration typically comprises a set of vectors P between selected points on registration marker 40 and selected vertebrae of patient 20. In one embodiment, the registration comprises using a 4×4 homogenous transformation, comprising a 3×3 rotation and a 1×3 translation, that transforms a point in the space of patient 20 to a point in registration marker frame of reference 50.

In a camera image analysis step 162, processor 32 analyzes the camera image of patient marker 38 and registration marker 40 acquired in step 156. From the acquired image, processor 32 calculates the position and orientation of registration marker frame of reference 50, and the position and orientation of patient marker frame of reference 36. Once the processor has calculated the positions and orientations of the two frames of reference, it formulates a registration of the two frames of reference as a set of vectors Q describing the transformation of the registration marker frame of reference to the patient marker frame of reference.

In a concluding analysis step 164, the processor adds the two sets of vectors found in steps 160 and 162 to formulate a registration set of vectors R between the patient marker frame of reference 36 and the patient anatomy, as shown in equation (1):

$$R = P + Q \tag{1}$$

Step 164 is the concluding step of the initial preparatory stage of the medical procedure referred to above.

FIG. 6 illustrates a subsequent stage of the medical procedure, corresponding to a final step 166 of the flowchart. In the subsequent stage, i.e., during the final step, registration marker 40 has been removed from the back of patient 20, and a medical professional 180 operates on the patient. Professional 180 wears an augmented reality head-mounted display (HMD) 184, which is configured to present stored images, that are aligned with the patient, to the professional. In order to operate, HMD 184 is coupled to processor 32 of system 28, or alternatively HMD 184 has its own dedicated processor which performs similar functions to those performed by processor 32.

To perform the alignment for HMD 184, the HMD projects visible or invisible light to patient marker 38, and acquires images of reflectors 106 of the marker. From the acquired images, the HMD processor determines the position and orientation of frame of reference 100 of the patient marker. The processor applies the registration set of vectors R, found in step 164, to the position and orientation of the marker frame of reference in order to ensure that the images projected by the HMD align with the anatomy of patient 20.

In some embodiments of the present invention, during step 166 one or more surgical tools used by professional 180 are tracked by the processor of HMD 184. By way of example, FIG. 6 illustrates a surgical tool 190 used by the professional, and the tool is tracked by the HMD processor, by having identifying reflectors 194, generally similar to reflectors 106, attached to the tool. From the tracking of the tool, the HMD processor is able to present an image of the tool (on HMD 184) that aligns with the actual tool, and the image may effectively make visible to the professional elements of the actual tool that may be hidden by the patient's anatomy.

During step 166 there may be situations where the positioning of patient marker 38 interferes with the actions of professional 180. Embodiments of the present invention accommodate this type of interference, by allowing the patient marker to be removed from clamp 30, and reattached in a different predetermined fixed spatial relationship with the clamp. Such a removal and reattachment of the marker with a rotation of 180° is described above with reference to FIG. 4, and the scope of the present invention includes removal and reattachment of the marker in any one of a plurality predetermined fixed spatial relationships.

In the case of embodiments comprising such a plurality predetermined fixed spatial relationships, processor 32 is configured, typically prior to implementation of step 166, to recognize the changed relationship of the patient marker with the clamp, and to compensate for the changed relationship.

An augmented reality head mounted display such as HMD 184 is described in more detail in U.S. Patent Application 2017/0178375 which is incorporated herein by reference. The application also describes making visible to a professional elements of an actual tool, used in a medical procedure, that may be hidden by the patient's anatomy.

In the description herein and in the claims, an entity having no axis of symmetry is assumed to have no rotational axis of symmetry other than a trivial rotational axis of symmetry of 360° or an integral multiple thereof. Also in the description herein and in the claims, a two dimensional entity having no plane of symmetry is assumed to have no mirror plane of symmetry other than a trivial mirror plane wherein the two dimensional entity lies.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

12

What is claimed is:

1. An apparatus comprising:
   a patient marker configured to be attached to a portion of a skeleton of a patient, the patient marker having a patient marker frame of reference;
   a registration marker comprising:
   a radiotransparent substrate,
   an optically visible pattern disposed on the radiotransparent substrate and arranged in at least two dimensions to have no axis of symmetry and no plane of symmetry, and
   a multiplicity of radiopaque elements disposed in the radiotransparent substrate and spatially arranged in the at least two dimensions to have no axis of symmetry and no plane of symmetry; and
   a processor, configured to:
   analyze an optical image of the patient marker and the registration marker, positioned in proximity to the patient marker, so as to determine a first relation between the patient marker frame of reference and a registration marker frame of reference, analyze a fluoroscopic image of the registration marker and the skeleton of the patient to determine a second relation between the registration marker frame of reference and the skeleton of the patient, and
   use the first relation and the second relation to formulate a registration relation between the patient marker and the skeleton.

2. The apparatus of claim 1, further comprising:
   a clamp and a removable screw,
   wherein:
   the portion of the skeleton of the patient is a portion of a spine,
   the clamp is configured to attach to one or more processes of the spine,
   the patient marker is further configured to connect to the clamp,
   the patient marker comprises a rectangular parallelepiped substrate to which is attached a tongue, and
   the removable screw is configured to fixedly connect the rectangular parallelepiped substrate of the patient marker to the clamp.

3. The apparatus of claim 2, wherein the patient marker is connected to the clamp in a predetermined fixed spatial relationship.

4. The apparatus of claim 2, wherein the patient marker is adapted to be connected to the clamp in a plurality of different predetermined fixed spatial relationships such that the patient marker can be removed, rotated, and re-connected.

5. The apparatus of claim 2, wherein the rectangular parallelepiped substrate of the patient marker comprises a solid opaque plastic material.

6. The apparatus of claim 2, wherein the optically visible pattern comprises discrete elements having a common size and shape, and wherein locations of the discrete elements are selected to form the optically visible pattern.

7. The apparatus of claim 2, wherein the optically visible pattern comprises a given discrete element having a first size and remaining discrete elements having a second size.

8. The apparatus of claim 2, wherein the optically visible pattern comprises a given discrete element having a first shape and remaining discrete elements having a second shape.

9. The apparatus of claim 2, wherein the patient marker further comprises a plurality of optically reflective elements attached to an upper two-dimensional surface of the rectangular parallelepiped substrate of the patient marker and arranged such that an optical pattern formed by the plurality of optically reflective elements enables the processor to determine an orientation and a position of the patient marker frame of reference from the optical image.

10. The apparatus of claim 2, wherein the fluoroscopic image is a computed tomography image of at least portion of the skeleton of the patient.

11. The apparatus of claim 2, wherein the second relation comprises a first set of vectors P between selected points on the registration marker and selected vertebrae of the portion of the skeleton of the patient.

12. The apparatus of claim 11, wherein the second relation comprises using a 4×4 homogenous transformation, comprising a 3×3 rotation and 1×3 translation.

13. The apparatus of claim 11, wherein the first relation is formulated as a second set of vectors Q describing a transformation of the registration marker frame of reference to the patient marker frame of reference.

14. The apparatus of claim 13, wherein formulation of the registration relation comprises adding the first set of vectors P and the second set of vectors Q to formulate a registration set of vectors R between the patient marker frame of reference and the portion of the skeleton.

15. The apparatus of claim 14, wherein the processor is further configured apply the registration set of vectors to a position and orientation of the patient marker frame of reference so that images projected by a head-mounted display device worn by a wearer align with the portion of the skeleton.

16. The apparatus of claim 1, wherein the radiotransparent substrate of the registration marker comprises a pillar attached to a rectangular parallelepiped, wherein the optically visible pattern of the registration marker comprises optically reflective discrete elements, and wherein one of the optically reflective discrete elements is mounted on the pillar.

17. The apparatus of claim 1, wherein the radiotransparent substrate of the registration marker comprises an indentation formed within a rectangular parallelepiped, wherein the optically visible pattern of the registration marker comprises optically reflective discrete elements, and wherein one of the optically reflective discrete elements is mounted on a surface of the indentation.

18. The apparatus of claim 1, wherein the optically visible pattern of the registration marker is formed in three dimensions and wherein the radiopaque elements of the registration marker are spatially arranged in three dimensions.

19. The apparatus of claim 1, wherein:

the radiotransparent substrate is optically opaque and comprises a surface, the optically visible pattern that is disposed in the at least two dimensions is disposed on the surface, the optically visible pattern that is disposed in the at least two dimensions on the surface comprises optically reflective discrete elements mounted on the surface, and the optically reflective discrete elements are different from the radiopaque elements.

20. The apparatus of claim 19, wherein:

the optically reflective discrete elements comprise discs, and the radiopaque elements comprise spheres.

* * * * *